United States Patent
Testa et al.

(10) Patent No.: US 6,958,215 B1
(45) Date of Patent: Oct. 25, 2005

(54) METHODS AND COMPOSITIONS FOR INHIBITION OF RNA SPLICING

(75) Inventors: Stephen M. Testa, Lexington, KY (US); Matthew D. Disney, Rochester, NY (US); Sergei M. Gryaznov, San Mateo, CA (US); Douglas H. Turner, Pittsford, NY (US)

(73) Assignees: Geron Corporation, Menlo Park, CA (US); The University of Rochester, Rochester, NY (US)

( * ) Notice: Subject to any disclaimer, the term of this patent is extended or adjusted under 35 U.S.C. 154(b) by 0 days.

(21) Appl. No.: 09/936,146

(22) PCT Filed: Mar. 15, 2000

(86) PCT No.: PCT/US00/07045

§ 371 (c)(1),
(2), (4) Date: Feb. 11, 2002

(87) PCT Pub. No.: WO00/55374

PCT Pub. Date: Sep. 21, 2000

Related U.S. Application Data
(60) Provisional application No. 60/124,451, filed on Mar. 15, 1999.

(51) Int. Cl.[7] .......................... C12Q 1/68; C12N 15/00; C12N 15/63; C12N 1/20; C12N 21/04

(52) U.S. Cl. ...................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Search ......................... 435/6, 91.1, 91.2, 435/91.21, 91.5, 91.51, 91.53, 184, 195; 536/24.33, 25, 34; 935/6, 8, 78, 17, 18; 436/518

(56) References Cited

U.S. PATENT DOCUMENTS 5,525,468 A * 6/1996 McSwiggen .................. 435/6
5,591,607 A    1/1997 Gryaznov et al.
5,631,135 A    5/1997 Gryaznov et al.
5,648,480 A * 7/1997 Letsinger et al. .......... 536/25.34
5,824,793 A    10/1998 Hirschbein et al.
5,849,484 A * 12/1998 Leibowitz et al. ............. 435/6
5,869,254 A * 2/1999 Sullenger et al.
6,180,339 B1 * 1/2001 Sandhu et al. ................. 435/6

OTHER PUBLICATIONS

Gryaznov, S.M., and H. Winter, "RNA Mimetics: Oligoribonucleotide N3'→P5' Phosphoramidates," *Nucleic Acids Research* 26(18):4160–4167, 1998.

Pongracz, K. and S. Gryaznov, "Oligonucleotide N3'→P5' Thiophosphoramidates: Synthesis and Properties," *Tetrahedron Letters* 40:7661–7664, 1999.

Gryaznov et al. J. Am.Chem. Soc. 1994, 116, 3143–3144.*

Liu et al., "Sequence and Variability of the 5.8S and 26S rRNA Genes of Pneumocystis Carinii," *Nucleic Acids Research* 20(14):3763–3772, 1992.

Testa et al., "In Vitro Suicide Inhibition of Self–Splicing of a Group I Intron from Pneumocystis Carinii by an N3'→P5' Phosphoramidate Hexanucleotide," *Proc. Natl. Acad. Sci. USA* 96:2734–2739, 1999.

* cited by examiner

Primary Examiner—Jeffrey Fredman
Assistant Examiner—Arun Chakrabarti
(74) Attorney, Agent, or Firm—Christensen O'Connor Johnson Kindness PLLC

(57) ABSTRACT

A method of inhibiting the self-splicing of a Group I intron is disclosed. The method uses an oligonucleotide having a sequence essentially identical to a guide sequence found in the 5' flanking exon and terminates with a 3' ribonucleoside. Usually the oligonucleotide has N3'→P5' phosphoramidate or N3'→P5' thiophiosphoramidate linkages rather than phosphodiester linkages. A method of inhibiting the growth of organisms having Group I intron, particularly certain pathogenic fungi including *P. carinii*, *C. albicans*, and *A. nidulans* using the oglionucleotide is also provided.

19 Claims, 7 Drawing Sheets

SEQUENCE LISTING

<160> NUMBER OF SEQ ID NOS: 9

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphoramidate linkages
<221> NAME/KEY: misc_feature
<222> LOCATION: (1)..(6)
<223> OTHER INFORMATION: Description of Combined DNA/RNA Molecule:
      Synthetic olignucleotide wherein nucleotides 1-5 are deoxyribo-
      nucleotde 6 is a ribonucleotide

<400> SEQUENCE: 1 atgacu                                                              6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphoramidate linkages
<221> NAME/KEY: misc_feature
<222> LOCATION: (1)..(6)
<223> OTHER INFORMATION: Description of Combined DNA/RNA Molecule:
      Synthetic oligonucleotide, nucleotides 1-5 are deoxynucleotides
      and ribonucleotide

<400> SEQUENCE: 2 gcctcu                                                              6

<210> SEQ ID NO 3
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphoramidate linkages
<221> NAME/KEY: modified_base
<222> LOCATION: (4)..(4)
<223> OTHER INFORMATION: t

<400> SEQUENCE: 3 gccucu                                                              6

<210> SEQ ID NO 4
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphoramidate linkages
<221> NAME/KEY: modified_base
<222> LOCATION: (4)..(4)
<223> OTHER INFORMATION: t

<400> SEQUENCE: 4 gacucu                                                              6

```
<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphoramidate linkages
<221> NAME/KEY: misc_feature
<222> LOCATION: (1)..(6)
<223> OTHER INFORMATION: Description of Combined DNA/RNA Molecule:
      Synthetic oligonucleotide wherein nucleotides 1-5 are deoxynucleo-
      tides is a ribonucleotide

<400> SEQUENCE: 5 cagtau                                                                    6

<210> SEQ ID NO 6
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphodiester linkages

<400> SEQUENCE: 6 ggucau                                                                    6

<210> SEQ ID NO 7
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphodiester linkages

<400> SEQUENCE: 7 gccucu                                                                    6

<210> SEQ ID NO 8
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      phosphodiester linkages

<400> SEQUENCE: 8 gacucu                                                                    6

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide wherein all of the intra-nucleotide linkages are
      thiophosphoramidate linkages
<221> NAME/KEY: misc_feature
<222> LOCATION: (1)..(6)
<223> OTHER INFORMATION: Description of Combined DNA/RNA Molecule:
      Synthetic oligonucleotide wherein nucleotides 1-5 are deoxynucleo-
      tides is a ribonucleotide

<400> SEQUENCE: 9 gcctcu                                                                    6
```

METHODS AND COMPOSITIONS FOR INHIBITION OF RNA SPLICING

CROSS-REFERENCE TO RELATED APPLICATION

This application claims the benefit of U.S. Provisional Application No. 60/124,451, filed Mar. 15, 1999.

ACKNOWLEDGEMENTS

This invention was supported in part by grants from the National Institutes of Health. The U.S. Government may have rights in this invention.

FIELD OF THE INVENTION

The present invention relates to methods and compositions for inhibiting the self-splicing of Group I introns and, particularly, to methods and compositions for inhibiting the growth of certain pathogenic organisms containing such Group I introns and the treatment of diseases or conditions caused by such pathogenic organisms.

BACKGROUND OF THE INVENTION

Most human therapeutics have been discovered by screening natural products. Synthetic organic chemistry has made it possible to synthesize such natural products and derivatives thereof in large quantities, thus broadening the range of compounds that can be used clinically (Gates et al., *J. Am. Chem. Soc.* 74:1109–1110 (1952); Wipf et al., *J. Am. Chem. Soc.* 117:558–559 (1995); Nicolaou et al., Nature 392:264–269 (1998)). Synthetic methodology coupled with the outpouring of protein structural information has also allowed rational design of completely new therapeutic compounds (Gait et al., *TIBTECH* 13:430–438 (1995); Skulnick et al., *J. Med. Chem.* 40:1149–1164 (1997)). Similarly, the recent explosion in nucleic acid sequence information is providing a knowledge base for structure-based targeting of RNA. The first generation of such therapeutics consists of antisense nucleic acids that bind mRNA through Watson-Crick base-pairing and thereby regulate translation (Chrissey, *Antisense Res. Dev.* 1:65–113 (1991); Baserga et al., Ed. (1992) *Antisense Strategies*; Annals of the New York Academy of Sciences 660; New York Academy of Sciences: New York). Nucleic acids used for antisense therapeutics, typically between 15–20 nucleotides long, suffer from a number of disadvantages including high cost of synthesis (Wagner et al., *Nature Biotechnology* 14:840–844 (1996)), lack of specificity (Herschlag, *Proc. Natl. Acad. Sci. U.S.A.* 88:6921–6925 (1991)) and instability in vivo. Some of these disadvantages can be overcome by designing oligonucleotides in which the phosphodiester moiety is replaced by a more stable linking group. Earlier work by the present inventors has shown that short oligonucleotides in which the phosphodiesters are replaced by phosphoramidates bind as tightly, if not more tightly, to a complementary sequence.

Many opportunistic pathogens, in particular, fungal pathogens, have RNA elements that can serve as molecular targets for pharmacological intervention. Group I introns are one example of such an RNA element. Many pathogenic fungi have Group I introns in critical structural RNAs, for example, in ribosomal RNAs (rRNA). RNAs containing Group I introns undergo a process of self-splicing to remove the intron to produce a functional RNA. This self-splicing process of Group I introns is well known. For a review of the Group I intron splicing process, as well as a discussion of the properties of Group I introns in general, see Cech, "Self-Splicing of Group I Introns", *Ann. Rev. Biochem.* 59:543 (1990). Group I introns contain a guanosine binding site and catalyze a reaction in which a guanosine (or a guanosine nucleotide) attacks the 5' residue of the intron to produce 5' exon and guanosine-intron-3' exon intermediates, which then further react to yield linear guanosine-intron and the spliced 5' exon-3' exon product. During the self-splicing reaction, a region of the RNA at the 3' end of the 5' exon is thought to pair with a complementary sequence within the intron (the internal guide sequence or IGS) to align the 5' splice site for reaction. FIG. 2 (right side panel A1 through C1) depicts this pairing and subsequent guanosine attack and cleavage followed by joining of the exons.

*Pneumocystis carinii* is an opportunistic pathogen that is a common cause of death in immunocompromised patients (Hughes, *Annu. Rev. Med.* 42:287–295 (1991); Steinberg, *Science* 266:1632–1634 (1994)). The large subunit ribosomal RNA (rRNA) precursor contains a Group I self-splicing intron (Testa et al., *Biochemistry* 36:15303–15314 (1997); Liu et al., *Nucleic Acids Res.* 20:3763–3772 (1992)) that provides a potential therapeutic target (Liu et al., (1992); Mei et al., *Bioorg. Med. Chem.* 5:1185–1195 (1997)) since self-splicing is required for assembly of active ribosomes (Nikolcheva et al., *RNA* 3:1016–1027 (1997)). Other pathogenic organisms, including *Candida albicans* (Mercure et al., *Nucleic Acids Res.* 21:6020–6027 (1993)) and *Aspergillus nidulans* (Netzker et al., *Nucleic Acids Res.* 10:4783–4790 (1982)), are also known to contain Group I introns, particularly within their rRNAs. Group I introns have not been found in humans to date. Earlier work of the present inventors showed that an oligonucleotide hexamer having a sequence that "mimics" the sequence of the putative 5' exon guide sequence of a *P. carinii* ribosomal RNA Group I intron can tightly bind to a derived ribozyme through base-pairing and tertiary interaction. However, the ability of the mimic to compete for binding to the IGS with the endogenous 5' exon guide sequence was not shown because the derived ribozyme used for this work did not contain the 5' exon guide sequence that is endogenous to the *P. carinii* rRNA precursor.

SUMMARY OF THE INVENTION

The present invention provides methods and compositions for inhibiting the self-splicing reaction of Group I introns using oligonucleotides having a 3' terminal ribonucleoside that mimic the 5' exon guide sequence. More specifically, a suicide inhibitor of a Group I intron self-splicing reaction is provided that has an inhibitor oligonucleotide having a polynucleotide sequence that binds to a 5' internal guide sequence of a precursor RNA containing a Group I intron, or to a portion thereof. The inhibitor oligonucleotide is capable of binding with the 5' internal guide sequence of the precursor RNA wherein the inhibitor oligonucleotide is trans-spliced to the 3' exon of the precursor RNA. In another aspect of the invention the oligonucleotides have modified internucleosidal linkages, such as, for example phosphoramidate or thiophosphoramidate linkages.

In another aspect, the present invention provides a method for inhibiting the growth of an organism containing a Group I intron. The growth inhibition method involves contacting a precursor RNA containing a Group I intron with an inhibitor oligonucleotide, wherein said inhibitor oligonucleotide is trans-spliced to a 3' exon sequence of the precursor RNA.

In yet another aspect of the invention, a method is provided for designing a suicide inhibitor of Group I intron splicing whereby a nucleotide sequence that is essentially identical to a 5' exon guide sequence and is present in the 5' exon flanking a Group I intron is chosen. An inhibitor oligonucleotide is then made based upon homology to the 5' exon guide sequence in the precursor RNA. The inhibitor oligonucleotide is made to have has a 3' terminal ribonucleotide.

In a further aspect, the present invention provides a method for treating a disease or condition caused by an organism containing a Group I intron. A patient suffering from the disease or condition is administered a therapeutically effective amount of a suicide inhibitor oligonucleotide of the present invention. In a particular aspect, the present invention provides a method for treating a disease or condition caused by certain pathogenic fungi, including *Pneumocystis carinii, Candida albicans* and *Aspergillus nidulans*. Pharmaceutical compositions comprising an inhibitor oligonucleotide are also provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
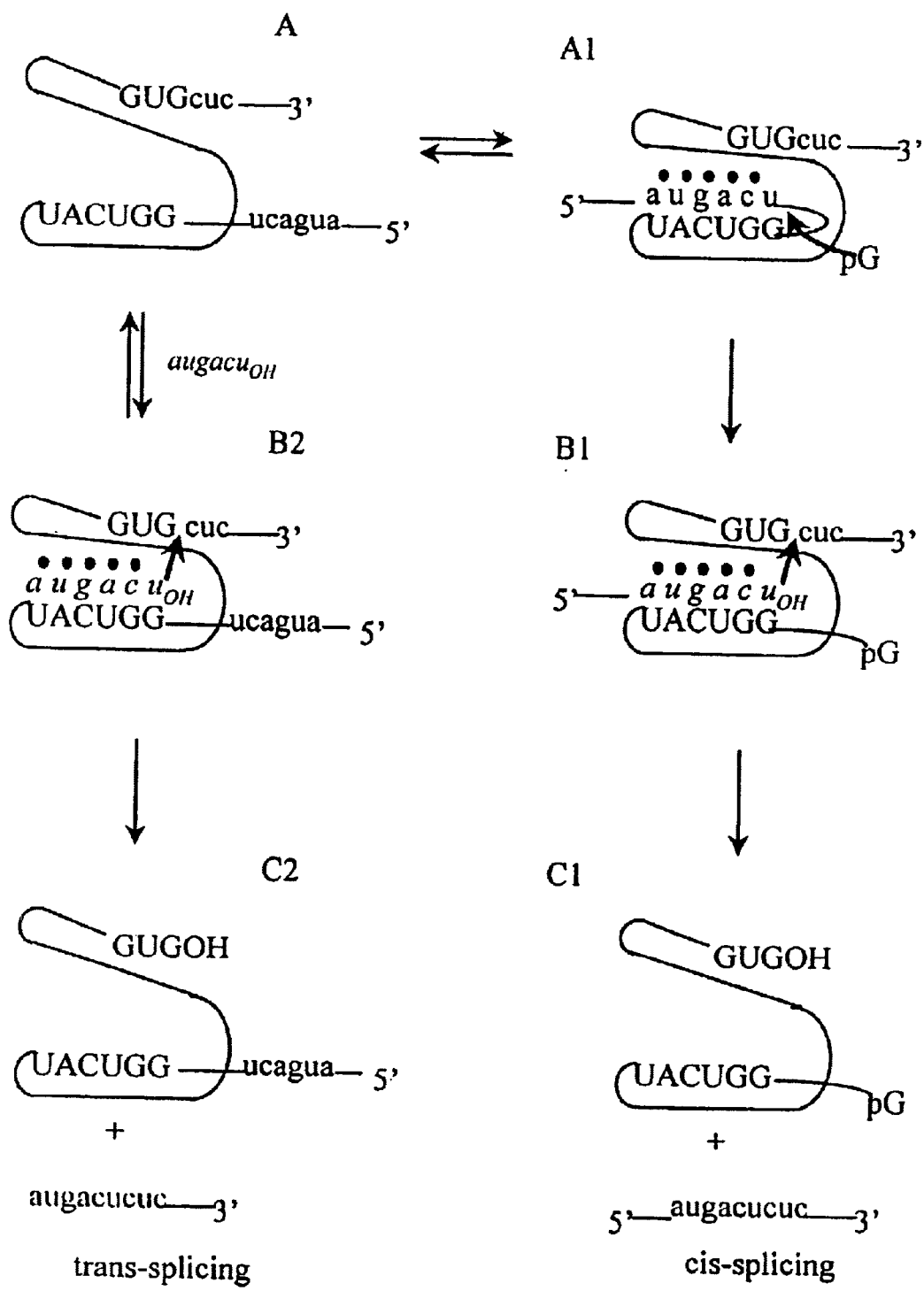
FIG. 1 is a schematic representation of the self-splicing (cis-splicing) and trans-splicing reactions of a Group I intron. The self-splicing reaction follows the pathway A→A1→B1→C1. The trans-splicing reaction follows the pathway A+agacu$_{OH}$→B2→C2. Steps B→C are essentially irreversible due to the low concentration of the spliced products. The upper case letters and intervening line represent the Group I intron; the lower case letters and terminal lines represent the 5' and 3' exons; the italicized lower case letters represent the exogenous N3'→P5' phosphoramidate hexanucleotide; filled circles represent tertiary interactions with the intron's catalytic site. The internal guide sequence (IGS) is shown as 5'-GGUCAU-3'.

The present inventors have discovered that a short oligonucleotide having a sequence that is essentially complementary to the IGS of a Group I intron and containing phosphoramidate and/or thiophosphoramidate linkages in place of phosphodiester linkages can inhibit the self-splicing reaction of Group I intron-containing RNAs, particularly the rRNA of *P. carinii*, thereby preventing the formation of functional, spliced RNA products. These inhibitor oligonucleotides ("IO") not only inhibit the self-splicing (or cis-splicing) reaction, but are participants in a trans-splicing reaction with the RNA precursor which results in the formation of dead-end spliced products. The IO thus function as "suicide inhibitors" of the Group I intron self-splicing reaction. These inhibitor oligonucleotides can be used in a method to inhibit the self-splicing reaction and thereby inhibit or impair the growth of the organism containing the Group I intron. Inhibitor oligonucleotides of the present invention are therefore useful in a method to treat any pathogenic condition resulting from the opportunistic growth of organisms containing Group I introns, particularly *P. carinii, C. albicans* and *A. nidulans.*

The notation used herein for the IO will be similar to that conventionally used to describe oligonucleotides, with the 5' most residue written at the left and the 3' most residue written at the right. Deoxyribonucleotide residues will be written "dX" and ribonucleotide residues will be written "rX", where "X" indicates the particular base present in the nucleotide residue. Nucleotide residues joined by a N3'→P5' phosphoramidate linkage will be written with "n" between, for example, (dA)n(dT)n(rU) indicates a trinucleotide having the sequence "ATU" where the A and T residues are deoxyribonucleotides, the U is a ribonucleotide and the residues are all joined by N3'→P5' phosphoramidate linkages. Phosphodiester linkages are indicated by the absence of any notation between the nucleotide residues, for example, (dA)(dT)(rU) indicates a trinucleotide identical to the one just described but having phosphodiester linkages rather than phosphoramidate. In an alternate version of this notation, the oligonucleotides may be written with parentheses enclosing any consecutive string of deoxyribonucleotides or of ribonucleotides with a "d" or "r" preceding the parenthesis. Thus, the trinucleotides indicated above as (dA)n(dT)n(rU) and (dA)(dT)(rU) could alternatively be written as d(AnTn)rU and d(AT)rU. The first system of notation will preferably be used herein.

The inhibitor oligonucleotides of the present invention may comprise deoxyribonucleotides or ribonucleotides, or modified forms thereof, or combinations of the foregoing. Preferably, the inhibitor oligonucleotides will comprise primarily deoxyribonucleotides except for the 3' terminal nucleotide. The 3' terminal nucleotide will be a ribonucleotide or similar moiety containing a 2',3' cis-diol or 2'-hydroxy, 3'-amino or 2'-amino, 3'-hydroxy (where 2' and 3' here refer conventionally to positions on the ribose ring moiety). The inhibitor oligonucleotides will preferably contain those bases that are normally found in DNA or RNA, that is, adenine (A), guanine (G), thymine (T), cytosine (C) and uracil (U), and may contain other bases such as 2,6 diaminopurine. The inhibitor oligonucleotides of the present invention will contain N3'→P5' phosphoramidate or N3'→P5' thiophosphoramidate linkages between adjacent nucleotide residues rather than the phosphodiester linkages typical of naturally occurring DNA and RNA, although some phophodiester linkages may be present. At least one N3'→P5' phosphoramidate linkage or N3→P5' phosphoramidate linkage will be present, typically more than one and more usually all linkages between adjacent nucleotide residues will be N3→P5' phosphoramidate linkages. Synthesis of N3'→P5' phosphoramidate oligonucleotides is well known in the art and has been disclosed, liter alia, in U.S. Pat. No. 5,837,835 and Gryaznov et al. (*J. Amer. Chem. Soc.*, 116:3143 (1994)). The synthesis of oligonucleotides containing N3'→P5' thiophosphoramidate linkages is also known and described in Pongracz et al. (*Tetrahedron Let.* 40:7661–7664 (1999)). The inhibitor oligonucleotides of the present invention may also be made with other types of modified internucleoside linkages such as, for example, methyl phosphonate linkages as described by U.S. Pat. No. 5,936,080.

The inhibitor oligonucleotides of the present invention may range in size from 3–20 nucleotides and are typically from 6–15 nucleotides, more usually from 6–10 nucleotides. However, it will be apparent to one of ordinary skill in the art that the size of the inhibitor oligonucleotide will be determined, at least in part, by the size of the IGS as described below.

The sequence of the inhibitor oligonucleotide is chosen to be essentially complementary to the internal guide sequence (IGS) of the Group I intron, the splicing of which is to be inhibited. The internal guide sequences for a number of Group I introns have been described, for example, Mercure et al., *Nucleic Acids Res.* 21:6020–6027 (1993); Netzker et al., *Nucleic Acids Res.* 10:4783–4790 (1982), and Damberger and Gutell, *Nucleic Acids Res.* 22:3508 (1994). Other internal guide sequences useful in the practice of the present invention may be determined by methods that are well known in the art, for example, by inspection of the sequence of the RNA or by use of the algorithm of Lisacek et al. (*J. Mol. Biol.* 235:1206 (1994). In general, the IGS will be within the Group I intron, near the 5' end of the intron and will have a sequence that is essentially complementary to a region in the flanking 5' exon, which region is referred to herein as the exon guide sequence or EGS. The EGS region is also known as the 5' side of P1 (see, Cech (1990)). The inhibitor oligonucleotide of the present invention is designed to be complementary to the IGS sequence. The inhibitor oligonucleotide will therefore be a "mimic" of the EGS, that is, the inhibitor oligonucleotide will have essentially the same sequence as the EGS since the EGS is itself complementary to the IGS. The term "complementary" is intended to have the usual meaning in the art, that is, that the bases of the inhibitor oligonucleotide will pair, in anti-parallel fashion, with the bases of the IGS to form a double stranded region. The base pairs formed will preferably be typical of those observed in naturally occurring DNAs and RNAs and include A with T or U, and G with C or U, and less preferably, C with A. Other base pairing is possible provided that a double stranded region with the IGS will result. Thus it will be apparent to one of ordinary skill in the art that the inhibitor oligonucleotide of the present invention may differ in sequence from the EGS in that the EGS, for example, may contain a U in some position whereas the IO may contain a T in the corresponding position and still maintain the requisite pairing with an A in the complementary position in the IGS. Likewise the IO may contain a C in the position corresponding to a U in the EGS, and so forth. Similarly, the EGS may contain ribonucleotides whereas the IO may contain deoxyribonucleotides or ribonucleotides, or modified forms thereof, particularly phosphoramidate forms. Typically, most known IGSs have a G at the 5' end and, when this occurs, the IO of the present invention will have a U at the 3' end, preferably a rU.

As discussed above, the IO for any particular Group I intron will be designed based on the sequences of the IGS and the EGS for that particular Group I intron. Preferably, the IO will be selected to have a sequence that is identical to the EGS, or a portion of the EGS. Alternatively, the IO may differ in sequence from the EGS but in most cases will be selected to maintain the ability to pair with the IGS. In some cases, the IO will have the sequence of only a portion of the EGS, as where, for example, the EGS is longer than approximately 6 bases, the IO may be selected to have the sequence of 6 consecutive bases in the EGS. Thus the IO may be shorter than the EGS sequence. In other cases, the IO may contain additional bases flanking the sequence of the EGS and thus the IO will be longer than the EGS. For example, the IO may contain additional nucleotides at the 5' and/or 3' ends to enhance its ability to bind to the IGS or to improve the specificity of the binding (that is, to eliminate or decrease binding to regions within the intron other than the IGS or to other RNAs or DNAs). Optimization of the sequence for any particular IO will be readily within the skill of one of ordinary skill in the art using the teachings disclosed herein. The present inventors have found that an IO of formula I below is particularly useful for inhibition of self-splicing of a Group I intron within a rRNA of *P. carinii*.

(dA)n(dT)n(dG)n(dA)n(dC)n(rU) [Seq. ID No:1]     (I)

In another embodiment of the invention, an IO of formula II below is of use in inhibiting self-splicing of a Group I intron within a rRNA of *C. albicans*.

(dG)n(dC)n(dC)n(dT)n(dC)n(rU) [Seq. ID No:2]     (II)

The ability of any particular IO to inhibit the self-splicing of a Group I intron can be tested in any of a variety of ways that are well known in the art, for example, in an in vitro splicing system as described herein in Example 1 for the rRNA of *P. carinii*. See for example, U.S. Pat. No. 5,849,484. Typically, the IO will be assayed for splicing inhibitory activity in vitro using as a substrate for the self-splicing reaction an appropriate precursor RNA containing a Group I intron flanked by the 5' and 3' exons to be joined by the cis-splicing reaction. Tile entire 5' exon or 3' exon need not be present as long as there is an amount sufficient to function as a cis-splicing substrate. The appearance of cis-splicing reaction products may be monitored on a denaturing polyacrylamide gel using standard protocols with radioactive substrate. The self-splicing reaction and inhibition assay is typically carried out in 50 mM Hepes (25 mM $Na^+$), 135 mM KCl, and $MgCl_2$ from 0 to 15 mM, preferably 1–3 mM. The splicing substrate RNA is annealed at approximately 55° C. for 5 min, then slow cooled to 37° C. pG is added to approximately 1 mM and IO from approximately 0–100 µM. The reaction is carried out at 37° C. for about 1 hr and stopped by addition of a stop buffer and the reaction products separated on a denaturing polyacrylamide gel. One of ordinary skill in the art will be competent to modify the above protocol as appropriate to the particular Group I intron substrate and IO combination used.

In one embodiment, the present invention provides a method for inhibiting the growth of an organism having a Group I intron in its RNA, by contacting the organism with a composition comprising the IO. One of ordinary skill in the art may readily identify those organisms that will be appropriate for application of the method of the present invention, as numerous organisms containing Group I introns have been identified (Damberger and Gutell (1994); Lisacek et al. (1994); Cech, T. R., in *The RNA World*, $1^{st}$ edition, Gesteland and Atkins, eds., pp. 239–263 (1993) Cold Spring Harbor Press). It will be readily apparent that the organisms most susceptible to the IO will be those in which the splicing of the Group I intron is critical to the function of some essential RNA species, for example, one of the ribosomal RNA subunits. In a particular embodiment, the method of the present invention may be used to inhibit the self-splicing of the rRNA of *P. carinii*. An IO of formula I is particularly useful in the practice of this method. In another embodiment, the method of the present invention may be used to inhibit the self-splicing of the rRNA of *C. albicans*. An IO of formula II is particularly useful in the practice of this method.

In yet another embodiment, the present invention provides a method for the treatment of a disease or condition resulting from the opportunistic growth of a pathogenic organism containing a Group I intron in its RNA, by administering to an individual suffering from such disease or condition, a therapeutically effective amount of a pharmaceutical composition comprising an IO. By "therapeutically effective amount" is meant an amount that relieves (to some extent) one or more symptoms of the disease or condition in the individual. Additionally, by "therapeutically effective amount" is meant an amount that returns to normal, either partially or completely, physiological or biochemical parameters associated with or causative of such a disease or condition. Generally, it is an amount between about 1 nmole and 1 mmole of the molecule, depending on the potency of the IO as determined in an in vitro self-splicing assay such as shown herein, and on other factors, such as, the age, size, and disease associated with the patient.

Preparation of such pharmaceutical compositions and appropriate treatment regimes will vary depending upon the particular disease or condition, the particular pathogenic organism and the particular IO selected. One of ordinary skill in the art will be competent to select appropriate formulations, dosages, treatment regimes given the general knowledge of such in the art and the specific disclosures herein. Protocols for testing the ability of compounds to inhibit the growth of pathogenic organism like *P. carinii* are well known in the art, see for example, U.S. Pat. Nos. 5,668,166 and 5,302,598.

Pharmaceutical Compositions

In therapeutic application, the IO are utilized in a manner appropriate for antisense therapy in general. For such therapy, the IO of the invention can be formulated for a variety of modes of administration, including systemic and topical or localized administration. Techniques and formulations generally may be found in Remington's Pharmaceutical Sciences, Meade Publishing Co., Easton, Pa.

Compositions for aerosol and enteral, especially oral, and for parenteral administration are especially preferred. The compositions comprise an inhibitor oligonucleotide alone or, preferably, together with a pharmaceutically acceptable carrier. The dosage of the IO depends upon the disease to be treated and upon the species, age, weight and condition of the individual to be treated, and also upon the mode of administration.

Preferred is a pharmaceutical composition suitable for administration to a warm-blooded animal, especially a human, suffering from a medical condition described herein, for example *P. carinii* pneumonia or *C. albicans*, comprising an IO described herein, or a salt thereof when salt-forming groups are present, in an amount effective for the inhibition of the splicing of the Group I intron, together with at least one pharmaceutically acceptable carrier. Suitable pharmaceutical formulations and methods for delivery of therapeutic nucleic acids have been abundantly described, see for example, U.S. Pat. Nos. 5,908,635, 5,855,911, 5,858,987, 5,593,974 and 5,294,533.

Preferably, the compounds of the invention are formulated for pulmonary administration. One such method of administration involves the aerosolization of a solution containing, preferably, an aqueous-soluble compound of the invention. Aerosol compositions can alternatively include the active compound packaged in reverse micelles or liposomes. Pharmaceutical compositions suitable for such a method of administration can additionally include aerosol propellants and a surfactant. Examples of small compounds administered by this method can be found in U.S. Pat. Nos. 5,364,615, 5,292,499, and 5,238,683. Both phospholipid and nonconventional liposomes are rapidly becoming accepted as pharmaceutical agents which improve the therapeutic value of a wide variety of compounds (*Cancer Res.* 43:4730 (1983)) and can be applied to inhibitor oligonucleotides identified by methods of the present invention.

Compounds with poor solubility in aqueous systems require formulation by using solubilizing agents such as ionic surfactants, cholates, polyethylene glycol (PEG), ethanol, or other agents which may have undesirable effects when used for inhalation. In addition, a treatment requiring successful delivery into alveoli of the lower pulmonary region may preclude from the formulation the use of certain irritants such as chlorofluorocarbons and should involve a minimum number of required doses. Alternatively, to avoid such limitations, liposomes or hydrophobic particles can be used. An inhalation formulation providing for a sustained release of such a compound using aerosol droplet particles approximately $1–2.1\mu$ in size, preferably less than $1\mu$, would satisfy these special needs.

Small particle aerosol liposomes and liposome-nucleic acid combinations for medical use are known in the art, see, for example, U.S. Pat. No. 5,858,784. Conventional liposomal formulations sometimes have an uncontrollable and fast release rate and frequently have larger particle sizes than are useful for directing a drug to alveoli. However, nonconventional liposomes, which are formed solely by cholesterol and cholesterol derivatives, or alternatively amphipathic lipid components, have been used successfully with controllable sustained release, improved solubility, high encapsulation, absence of need for multiple dosing, and extended stability. Suitable liposomal formulations for sustained release of such compounds include sodium cholesterol sulfate:cholesterol:compound % molar ratios of 55:40:5, 50:40:10; 53:37:9, and most preferably 50:40:10 (U.S. Pat. No. 5,049, 389).

The pharmaceutical compositions comprise from approximately 5% to approximately 95% active ingredient, dosage forms in single dose form preferably comprising from approximately 20% to approximately 90% active ingredient and dosage forms that are not in single dose form preferably comprising from approximately 5% to approximately 20% active ingredient Unit dose forms, such as degrées, tablets or capsules, comprise from approximately 0.01 mg to approximately 10.0 mg of active ingredient.

The pharmaceutical compositions of this invention are prepared in a manner known per se, for example by means of conventional mixing, granulating, confectioning, dissolving or lyophilizing processes. For example, pharmaceutical compositions for oral use can be obtained by combining the active ingredient with one or more solid carriers, optionally granulating a resulting mixture, and, if desired, processing the mixture or granules, if appropriate with the addition of additional excipients, to form tablets or dragée cores.

Suitable carriers include fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical compositions also include dry-filled capsules consisting of gelatin, and also soft, scaled capsules consisting of gelatin and a plasticizer, such as glycerol or sorbitol. The dry-filled capsules may contain the active ingredient in the form of granules, for example in admixture with fillers, such as corn starch, binders and/or gildants, such as talc or magnesium stearate, and optionally stabilizers. In soft capsules, the active ingredient is preferably dissolved or suspended in suitable liquid excipients, such as fatty oils, paraffin oil, liquid polyethylene glycols or fatty acid esters of ethylene or propylene glycol, to which stabilizers and detergents, for example of the polyoxethylen-sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

For parenteral administration compositions include suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophlilisate and can be made into a solution prior to parenteral administration by the addition of suitable solvents. Solutions such as those that are used, for example, for parenteral administration can also be used as infusion solutions.

For topical administration, particularly cosmetic formulations, the IO of the invention are formulated into ointments, salves, gels, or creams as generally known in the art

EXAMPLES

The following examples are offered by way of example and not by way of limitation. Variations and alternate embodiments will be apparent to those of ordinary skill in the art.

Example 1

Materials and Methods

DNA and RNA Synthesis and Purification. The truncated *P. carinii* rRNA precursor (P-h), the derived ribozyme (P-8/4x), the derived *C. albicans* ribozyme (C-10/1x), and hexanucleotides were synthesized and purified essentially as described (Testa et al., *Biochemistry* 36:15303–15314 (1997); Gryaznov et al., *J. Am. Chem. Soc.* 116:3143–3144

(1994)). Hexamers were 5' end radiolabeled and the P-h rRNA precursor was internally radiolabeled as previously described (Testa et al., Biochemistry 36:15303–15314 (1997)).

The P-h rRNA precursor was 3' end radiolabeled by incubating 1 µM [5'-$^{32}$P] pCp, 440 nM P-h RNA transcript, 10 mM MgCl$_2$, 5 µM ATP, 3 mM DTT, 250 ng BSA, 50 mM Hepes (pH 8.3), and 30 units T4 RNA ligase in a total volume of 25 µL for 5 h at 22° C. The reaction mixture was passed through a chromaspin G 100 size-exclusion spin column (CLONTECH Laboratories Inc., Palo Alto, Calif.) to remove unincorporated [5'-$^{32}$P] pCp, and then added to 12.5 µL of 2x stop buffer (10 M urea, 3.1 mM EDTA, 10 mM Tris, and 9 mM Boric Acid at pH 8.4) and 2 µL glycerol. The labeled precursor was purified on a 5% polyacrylamide, 8M urea denaturing gel. The precursor band was excised from the gel and eluted by pulverizing at room temperature overnight in 1 mL sterile water with a sterile, stir bar (the spin-soak procedure). The resultant solution was spin filtered (Isolab, Inc. Akron, Ohio) to remove gel particulate and ethanol precipitated twice to remove residual salts and urea.

Inhibiting of Self-Splicing. Reactions were conducted in HxMg buffer consisting of 50 mM Hepes (25 mM Na$^+$), 135 mM KCl, and x mM MgCl$_2$ at pH 7.5, where x refers to the amount of MgCl$_2$ in mM in the buffer (listed in the FIGUREs). For *P. carinii* splicing reactions conducted with internally radiolabeled precursor RNA, about 180 nM of the RNA was reannealed at 55° C. for 5 min in the appropriate buffer in a volume of 3 µL and then slow cooled to 37° C. A 3 µL solution of buffer at 37° C. containing either 2 mM pG and/or 60 µM (dA)n(dT)n(dG)n(dA)n(dC)n(rU) [Seq. ID No:1] or neither was added and allowed to react for 1 h at 37° C. An equal volume of 2x stop buffer was added and the products and reactants separated on a 5% acrylamide, 8 M urea gel. To check sequence specificity, the self-splicing reaction was conducted with the control oligonucleotide (dC)n(dA)n(dG)n(dT)n(dA)n(rU) [Seq. ID No:5] as above using H2Mg buffer and 1 mM pG, conditions that maximize production of the 5' exon-intron band with (dA)n(dT)n(dG)n(dA)n(dC)n(rU) [Seq. ID No:1]. Gels were dried under vacuum and the bands quantified on a Molecular Dynamics phosplorimager. The intensity of each band was corrected for the number of adenines in each sequence. A final concentration of 1 mM pG was used in these assays because 3 mM pG, although resulting in marginally more spliced product, also doubles the amount of 5' exon-intron hydrolysis product. The same reaction conditions were used to test the efficacy of *C. albicans* hexamers in the inhibition of a model precursor rRNA from *C. albicans* (see Example 3).

The fate of the hexamers, (dA)n(dT)n(dG)n(dA)n(dC)n(rU) [Seq. ID No:1] and (dC)n(dA)n(dG)n(dT)n(dA)n(rU) [Seq. ID No:5], was also analyzed using radiolabeled hexamer and unlabeled precursor in the presence and absence of pG colactor. Approximately 300 nM unlabeled P-h precursor was reannealed at 55° C. in 3 µL of the appropriate buffer for 5 min and slow cooled to 37° C. A 3 µL solution of 8 mM 5' end radiolabeled hexamer in the same buffer at 37° C. was added and the reaction was allowed to proceed for 1 h. The reaction was quenched by the addition of 6 µL of 2x stop buffer and the reactants and products were separated on a 10% polyacrylamide, 8 M urea gel. The gel was dried under vacuum and the bands quantified with a Molecular Dynamics phosphorimager.

To directly monitor the cis and trans-spliced products, the self-splicing reaction was analyzed as a function of (dA)n(dT)n(dG)n(dA)n(dC)n(rU) [Seq. ID No:1] concentration using 3' end radiolabeled P-h precursor. The reaction was conducted essentially as described using internally radiolabeled precursor RNA, except that the concentration of (dA)n(dT)n(dG)n(dA)n(dC)n(rU) [Seq. ID No:1] ranged from 10 nM to 30 µM, the concentration of precursor was approximately 5 nM, and H4Mg buffer was used. Bands were identified by their migration relative to the precursor, the 3' exon hydrolysis product, and the properly spliced product bands (the latter two determined in the absence of added hexamer).

P8/4x Ribozyme Binding Assays. The dissociation constant for (dA)n(dT)n(dG)n(dA)n(dC)n(rU) [Seq. ID No:1] binding to the P-8/4x ribozyme was determined by direct band-shift polyacrylamide gel electrophoresis assays using H15Mg, H5Mg, and H3Mg as the binding and electrophoresis buffers (Testa et al., Biochemistry 36:15303–15314 (1997)). In these assays, 6.56 µL of serially diluted P-8/4x ribozyme at concentrations ranging from 0.005 to 1.5 µM in the appropriate buffer with 3.4% glycerol (v/v) were incubated at 55° C. for 5 min and then slowly cooled to 37° C. Approximately 8 nM of $^{32}$P radiolabeled 5' exon mimic, (dA)n(dT)n(dG)n(dA)n(dC)n(rU) [Seq. ID No:1], in 0.94 µL of the appropriate buffer at 37° C. was added and the solution allowed to equilibrate for 90 min. The fraction of mimic bound was partitioned from unbound on a 37° C., 10% native polyacrylamide gel, which was made with the same buffer as the binding buffer. The gel was then dried under vacuum and the bands quantified with a Molecular Dynamics phosphorimager. Dissociation constants were calculated as previously described (Testa, et al., Biochemistry 36:15303–15314 (1997)).

Example 2

*Pneumocystis carinii* Results

Reactivity of Internally Radiolabeled Precursor as a Function of [Mg$^{2+}$]. The effects of Mg$^{2+}$ concentration on the formation of various products derived from internally radiolabeled precursor RNA in the presence and absence of 30 µM (dA)n(dT)n(dG)n(dA)n(dC)n(rU) [Seq. ID No:1] and 1 mM pG are shown in FIGS. 2A–B. FIG. 2A shows that in the presence of (dA)n(dT)n(dG)n(dA)n(dC)n(rU) [Seq. ID No:1] and pG, the 5' exon-intron product reaches a maximum at 2 mM Mg$^{2+}$, where it is 7.5-fold more prevalent than the completely excised intron product. Mg$^{2+}$ concentrations higher than 3 mM, however, result in a predominance of completely excised intron. The 5' exon-intron product could arise from either trans-splicing of (dA)n(dT)n(dG)n(dA)n(dC)n(rU) [Seq. ID No:1] or hydrolysis of the precursor at the intron-3' exon junction.

FIG. 2B shows results in the presence of 1 mM pG and absence of (dA)n(dT)n(dG)n(dA)n(dC)n(rU) [Seq. ID No:1]. When [Mg$^{2+}$]≧4 mM, the fraction of 5' exon-intron band is the same in the presence (FIG. 2A) and absence (FIG. 2B) of (dA)n(dT)n(dG)n(dA)n(dC)n(rU) [Seq. ID No:1]. Thus, when [Mg$^{2+}$]≧4 mM, the 5' exon-intron band is likely due to hydrolysis at the intron-3' exon junction. At 2 and 3 mM Mg$^{2+}$, however, much more 5' exon-intron product is formed in the presence of (dA)n(dT)n(dG)n(dA)n(dC)n(rU) [Seq. ID No:1], suggesting it results either from the trans-splicing reaction or from oligonucleotide induced hydrolysis at the intron-3' exon junction. Either mechanism results in the formation of oligonucleotide dependent dead end RNA products that cannot mature into normal splice products. At 2 mM Mg$^{2+}$ the fraction of completely excised intron decreases 2.5 fold upon adding 30 µM (dA)n(dT)n(dG)n(dA)n(dC)n(rU) [Seq. ID No:1] (compare FIGS. 2A and 2B), suggesting that the dead end products are, at least in part, being formed at the expense of completely excised intron. Surprisingly, the fraction of completely excised intron is almost 0.6 when $[Mg^{2+}] \geq 5$ mM in the presence of 30 μM (dA)n(dT)n(dG)n(dA)n(dC)n(rU) [Seq. ID No:1] and 1 mM pG, whereas it is only 0.4 when pG is present in the absence of (dA)n(dT)n(dG)n(dA)n(dC)n(rU) [Seq. ID No:1]. One possible reason for this is that (dA)n(dT)n(dG) n(dA)n(dC)n(rU) [Seq. ID No:1] promotes hydrolysis at both the 5' exon-intron and intron-3' exon junctions, thus releasing intron.

When the in vitro splicing assay was performed in the presence of (dA)n(dT)n(dG)n(dA)n(dC)n(rU) [Seq. ID No:1] and absence of pG, the fraction of excised intron approaches 0.2 at high $[Mg^{2+}]$ (FIG. 2C). When added to the 0.4 fraction generated in the presence of pG and absence of (dA)n(dT)n(dG)n(dA)n(dC)n(rU) [Seq. ID No:1], this can account for the fraction observed in the presence of both pG and (dA)n(dT)n(dG)n(dA)n(dC)n(rU) [Seq. ID No:1]. The same experiment also showed that in the absence of pG and presence of 30 μM (dA)n(dT)n(dG)n(dA)n(dC)n(rU) [Seq. ID No:1], the 5' exon-intron product maximized at 2 mM $Mg^{2+}$ (data not shown). Evidently, formation of this product does not depend on pG. At 3 mM $\leq [Mg^{2+}] \leq 7$ mM in the presence of 1 mM pG and 30 μM (dA)n(dT)n(dG)n(dA)n (dC)n(rU) [Seq. ID No:1], completely excised intron product was generated at the expense of the 5' exon-intron product (FIG. 2A).

In the absence of pG and (dA)n(dT)n(dG)n(dA)n(dC)n (rU) [Seq. ID No:1], hydrolytic production of the 5' exon-intron band at 2 mM $Mg^{2+}$ was about 10 times less than in the presence of (dA)n(dT)n(dG)n(dA)n(dC)n(rU) [Seq. ID No:1] (FIG. 2D). This is further evidence that the large production of this band was not the result of simple hydrolysis at the intron-3' exon splice junction.

The above results indicate that (dA)n(dT)n(dG)n(dA)n (dC)n(rU) [Seq. ID No:1] interferes with self-splicing at 2–3 mM $Mg^{2+}$ either by trans-splicing or by oligonucleotide-induced hydrolysis at the intron-3' exon junction or both. An increase in the 5' exon-intron product at 2 mM $Mg^{2+}$ does not occur upon adding up to 30 μM of the control hexamer (dC)n(dA)n(dG)n(dT)n(dA)n(rU) [Seq. ID No:5] instead of (dA)n(dT)n(dG)n(dA)n(dC)n(rU) [Seq. ID No:1], suggesting the effects are dependent on sequence complementarity between the oligonucleotide and the intron's internal guide sequence.

In contrast to the results at 37° C., at 50° C. the 5' exon-intron product predominates in H15Mg buffer, suggesting the 5' exon-intron product is favored under conditions that are expected to destabilize the Group I intron structure (data not shown).

Figure 3:
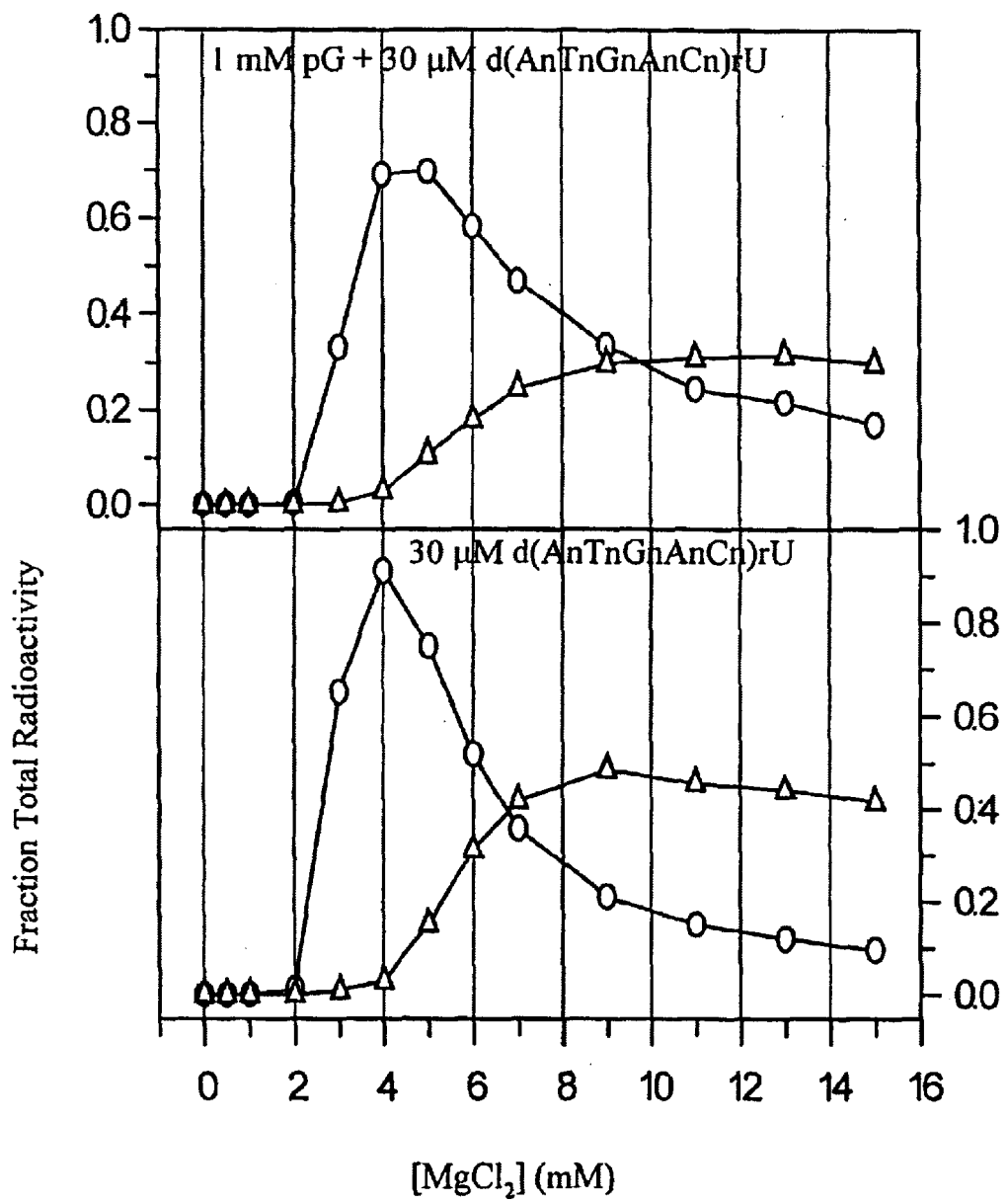
FIG. 3 shows graphical representations of the magnesium dependence of the trans-splicing reaction with 4 nM 5'end-labeled (dA)n(dT)n(dG)n(dA)n(dC)n(rU) [Seq. ID. No:1] and 150 nM unlabeled precursor in the presence (top) and absence (bottom) of pG. Reactions were run for 1 h in HxMg buffer, consisting of 50 mM Hepes (25 mM Na$^+$) at pH 7.5, 135 mM KCl, and x mM MgCl$_2$, where x is listed below the plot. Circles represent the hexamer-3' exon trans-spliced product at 33 nucleotides and triangles represent the unidentified ≈350 nucleotide product.

Reactivity of 5' End Radiolabeled Hexamer as a Function of $[Mg^{2+}]$. To directly monitor the trans-splicing product, 5' radiolabeled (dA)n(dT)n(dG)n(dA)n(dC)n(rU) [Seq. ID No:1] or d(CnAnGnTnAn)rU [Seq. ID No:5] was added to solutions of unlabeled precursor. FIG. 3 shows that the 5' exon mimic, (dA)n(dT)n(dG)n(dA)n(dC)n(rU) [Seq. ID No:1], is incorporated into two products; one is 33 nucleotides in length corresponding to the expected trans-spliced product, and one is approximately 350 nucleotides (the origin of this product is unknown at present). Formation of the trans-spliced product in the presence of pG is maximal at 4–5 mM $Mg^{2+}$ and then gradually decreases with increasing $Mg^{2+}$ (FIG. 3, top plot), which corresponds to a gradual increase in formation of the 350-mer product. This trend also holds when the assay is conducted in the absence of pG (FIG. 3, bottom plot), indicating that pG is not required for formation of either product. The control, (dC)n(dA)n(dG)n (dT)n(dA)n(rU) [Seq. ID No:1], is not reactive in 0, 2, 3, or 15 mM $Mg^{2+}$, as expected, showing that the reactions are sequence dependent.

Figure 4:
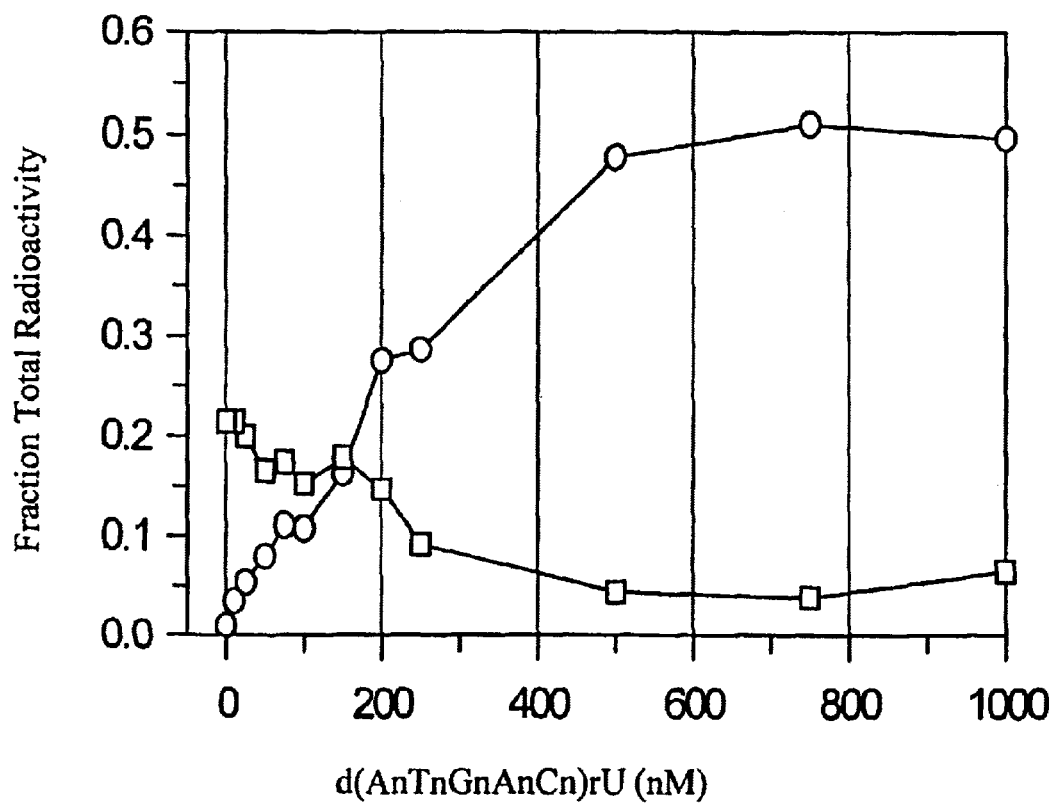
FIG. 4. Oligonucleotide concentration dependence of self-splicing (cis-splicing) and trans-splicing. Reactions consisted of approximately 6 nM 3' end radiolabeled precursor, 1 mM pG, H4Mg buffer, and various concentrations of (dA)n(dT)n(dG)n(dA)n(dC)n(rU) [Seq. ID. No:1] (listed in nM below the graph). Circles represent the hexamer-3' exon trans-spliced product and squares represent the 5' exon-3' exon cis-spliced product. The fractions of the trans-spliced and cis-spliced products are 0.74 and 0.01 at 30 μM (dA)n(dT)n(dG)n(dA)n(dC)n(rU) [Seq. ID. No:1].

Reactivity of 3' End Radiolabeled Precursor as a Function of (dA)n(dT)n(dG)n(dA)n(dC)n(rU) [Seq. ID No:1] Concentration at 4 mM $Mg^{2+}$. To directly monitor both cis and trans-splicing products, a 3' end radiolabeled precursor was used. With 3' end radiolabeled precursor, $Mg^{2+}$ dependent trans-splicing reaches a plateau at 4 mM $Mg^{2+}$. Therefore, the dependence of trans-splicing with 3' end radiolabeled precursor on (dA)n(dT)n(dG)n(dA)n(dC)n(rU) [Seq. ID No:1] concentration was analyzed at 4 mM $Mg^{2+}$ (FIG. 4). Inspection of the self-splice products on a gel showed that the second fastest migrating band in was the 33-mer trans-spliced product, and its formation depended on oligonucleotide concentration, as expected. Further, the 27-mer 3' exon hydrolysis product was also found to be distinguishable from the 33-mer trans-spliced product and its formation was independent of oligonucleotide concentration. The trans-spliced product plateaus at about 500 nM (dA)n(dT)n(dG) n(dA)n(dC)n(rU) [Seq. ID No:1], and the amount of trans-spliced product is greater than the amount of properly spliced product at concentrations of (dA)n(dT)n(dG)n(dA) n(dC)n(rU) [Seq. ID No:1] as low as 200 nM (FIG. 4). Since the $K_d$ for (dA)n(dT)n(dG)n(dA)n(dC)n(rU) [Seq. ID No:1] binding to the internal guide mimic, (rG)(rG)(rU)(rC)(rA) (rU) [Seq. ID No:6], is 34 μM (incorrectly reported as 340 μM in Table I of Testa et al., *Biochemistry* 37:9379–9385 (1998)) under the more stabilizing conditions of H15Mg buffer, the exon mimic is likely binding to the precursor at least partially through tertiary interactions. A trans-spliced product is not formed with up to 30 μM of the control oligonucleotide, (dC)n(dA)n(dG)n(dT)n(dA)n(rU) [Seq. ID No:5], indicating that the reaction is sequence specific.

$Mg^{2+}$ Dependence of (dA)n(dT)n(dG)n(dA)n(dC)n(rU) [Seq. ID No:1] Binding to the P-8/4x Ribozyme. To examine the effects of $Mg^{2+}$ concentration on the binding of (dA)n (dT)n(dG)n(dA)n(dC)n(rU) [Seq. ID No:1] to the catalytic core, binding was measured to the P-8/4x ribozyme, which is precursor truncated to remove 5' and 3' splice sites (Testa et al., (1998)). The dissociation constant at 3 mM $Mg^{2+}$ is roughly 2-fold and 6-fold larger than those at 5 and 15 mM $Mg^{2+}$, respectively (Table 1).

TABLE I $MgCl_2$ Dependence of Binding
(dA)n(dT)n(dG)n(dA)n(dC)n(rU)[Seq. ID No: 1] and P-8/4x

| $[MgCl_2]$ (mM) | $K_d$ (nM) |
| --- | --- |
| 3 | 175 |
| 5 | 99 |
| 15 | 31 (16)[1] |
| 4 | 94 |

Assays were run in HxMg buffer, consisting of 50 mM Hepes (25 mM Na⁺) at pH 7.5, 135 mM KCl, and x mM $MgCl_2$. Each reported value is the average of two independent assays. The dissociation constant, $K_d$, was determined by direct band-shift gel electrophoresis.

The reactivity of the exogenous 5' exon mimic (dA)n(dT) n(dG)n(dA)n(dC)n(rU) [Seq. ID No:1] with precursor RNA indicates that the mimic binds to the catalytic core of the Group I intron in the presence of the endogenous exons at about 2 mM $Mg^{2+}$ for the assay using internally labeled precursor and about 4 mM $Mg^{2+}$ for the other assays. Such $Mg^{2+}$ concentrations are essentially physiological (Hamson et al., (1980) In *Metals in Biochemistry*, Chapman and Hall., New York. pp. 8–9; Maquire, (1990) In Sigel. H. and Sigel. A. (eds), *Metals in Biological Systems* 26, Marcel Dekkar Inc., New York. pp. 135–153). The difference in the $Mg^{2+}$ dependence of trans-splicing between assays may be the result of structural heterogeneity of the precursor that differs due to different protocols for preparing unlabeled, internally radiolabeled, and 3' end radiolabeled precursor. Such structural heterogeneity is commonly seen for pre-rRNA transcripts and ribozymes (Lin et al., *Gene* 119:163–173 (1992); Bevilacqua et al., *Biochemistry* 30:10632–10640 (1991); Emerick et al., *Biochemistry* 32:14062–14067 (1993); Uhlenbeck, *RNA* 1:4–6 (1995); Pan et al., *J. Mol. Biol.* 276:7–13 (1997)). Attempts to produce more homogeneous solutions using published protocols (Emerick (1993); Uhlenbeck, (1995)) did not alter these results. Nevertheless, at low $Mg^{2+}$ concentrations, (dA)n(dT)n(dG)n(dA)n(dC)n(rU) [Seq. ID No:1] is spliced in trans to the endogenous 3' exon of the precursor in a reaction that mimics the second step of splicing (FIGS. 2, 3, and 4), and this reduces the amount of properly spliced product. Thus, this hexamer is a suicide inhibitor of the self-splicing reaction.

As shown in FIG. 4, the fraction of precursor RNA that is trans-spliced is half maximal at 200 nM (dA)n(dT)n(dG)n (dA)n(dC)n(rU) [Seq. ID No:1] in 4 mM $Mg^{2+}$. At 4 mM $Mg^{2+}$ (dA)n(dT)n(dG)n(dA)n(dC)n(rU) [Seq. ID No:1] effectively competes with the intramolecular 5' exon sequence for binding in the catalytic pocket. This is surprising since intramolecular binding has a considerable effective concentration advantage over bimolecular binding (Jencks, *Catalysis in Chemistry and Enzymology* (1987), Dover Publications, New York).

Figure 2:
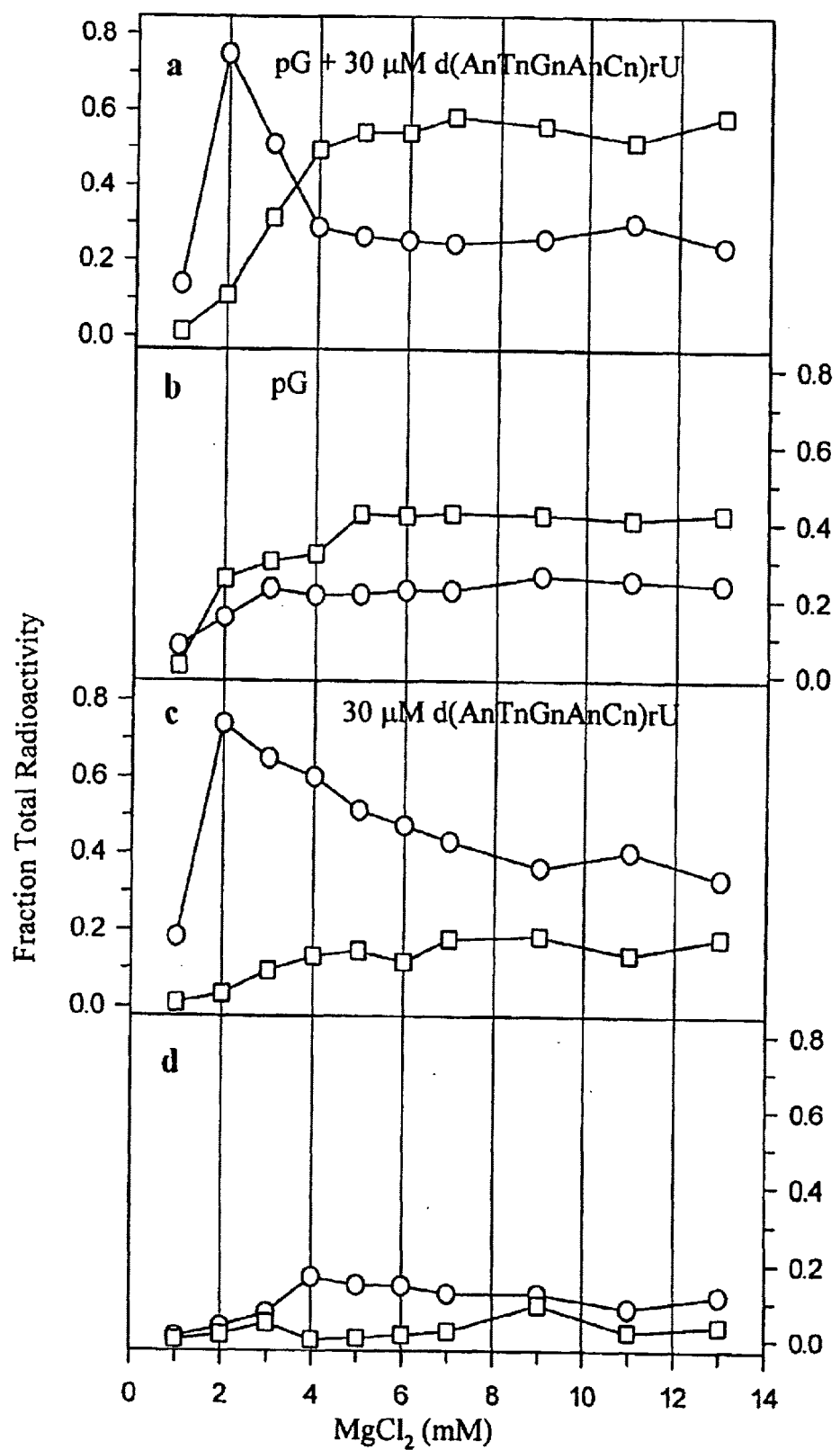
FIG. 2 shows graphical representations of the magnesium dependence of the formation of splice products from internally radiolabeled precursor. Reactions were run for 1 h in HxMg buffer, consisting of 50 mM Hepes (25 mM Na$^+$) at pH 7.5, 135 mM KCl, and x mM MgCl$_2$, where x is listed below the plots. Each plot is the average of two independently run self-splice gel assays, and the error of each point is typically ±6% of the average value. Circles represent the 5' exon-intron product generated by either trans-splicing or intron-3' exon junction hydrolysis. Squares represent the intron products formed either by splicing or by hydrolysis at both the 5' exon-intron and intron-3' exon junctions. Results are shown (A) in the presence of 1 mM pG and 30 μM (dA)n(dT)n(dG)n(dA)n(dC)n(rU) [Seq. ID. No:1], and (B) in the absence of added hexamer, (C) in the absence of pG and in the presence of 30 μM (dA)n(dT)n(dG)n(dA)n(dC)n(rU), and (D) in the absence of pG and (dA)n(dT)n(dG)n(dA)n(dC)n(rU).

It was previously reported that the dinucleotide monophosphate r(CU) in 5 mM $Mg^{2+}$ at 30° C. (Inoue et al., *Cell* 43:431–437 (1985)) and r(CCCCN) (where N is U, C, or A) in 10 mM $Mg^{2+}$ at 42° C. (Barfod et al., *Mol. Cell. Biol.* 9:3657–3666 (1989)) trans-splice with the natural *Tetrahymena thermophila* ribosomal RNA precursor in the absence of pG. Moreover, in 5 mM $Mg^{2+}$ at 30° C. in the presence of pG, the 3' terminal end of the 5' exon of the Group I intron from *T. thermophilia* can base-pair with upstream exon sequences, allowing exogenous 5' exon mimics to bind the internal guide sequence and act as trans-splicing substrates (Woodson et al., *Biochemistry* 30:2042–2050 (1991)). The 3' end of the *P. carinii* 5' exon can also form such an upstream structure, but the predicted thermodynamics suggest that it is significantly weaker than the structure with the 3' end of the 5' exon base-pairing to the internal guide sequence (−7 vs −3 kcal/mol). Indeed, using internally radiolabeled precursor, when $[Mg^{2+}]>3$ mM, the completely excised intron product predominates in the presence of pG and (dA)n(dT)n(dG)n(dA)n(dC)n(rU) [Seq. ID No:1], suggesting that under these conditions formation of the intramolecular 5' exon-internal guide sequence helix is favored (FIGS. 2 and 3). With internally labeled precursor at 2–3 mM $Mg^{2+}$, however, the internal guide sequence appears more accessible because more 5' exon-intron product is formed than completely excised intron, as expected if trans-splicing predominates.

The internal guide sequence may be more accessible at low $Mg^{2+}$ concentrations because the intron may not be completely or properly folded. Intracellular $Mg^{2+}$ concentrations are often less than 2 mM (Hamson et at., (1980) In *Metals in Biochemistry*, Chapman and Hall., New York. pp. 8–9; Maquire, (1990) In Sigel. H. and Sigel. A. (eds), *Metals in Biological Systems* 26, Marcel Dekkar Inc., New York, pp. 135–153) and cases are known where proteins are required to stabilize or catalyze proper folding of Group I introns (Weeks et al., *Cell* 82:221–230 (1995)). Thus there may be windows of opportunity in the cell for exogenous oligonucleotides to bind the intron during transcription or before a chaperone/folding protein has trapped the intron into its active three-dimensional structure.

The N3'→P5' phosphoramidate linkages in (dA)n(dT)n (dG)n(dA)n(dC)n(rU) [Seq. ID No:1] are resistant to chemical and nuclease degradation, a requirement for an effective therapeutic (Gryaznov et al., *J. Am. Chem. Soc.* 116:3143–3144 (1994); Gryaznov et al., *Nucleic Acids Res.* 24:1508–1514 (1996); Escudé et al., *Proc. Natl. Acad. Sci. U.S.A.* 93:4365–4369 (1996); Skorski et al., *Proc. Natl. Acad. Sci. U.S.A.* 94:3966–3971 (1997)). The results show that the oxygen to amino and 2' OH to 2' H functional group modifications permit both binding and trans-splicing. Moreover, the oligonucleotide effectively competes with the 5' exon for binding the catalytic core at low $Mg^{2+}$ concentrations. Other phosphoramidate oligonucleotides are known to bind tightly to RNA binding proteins (Rigl et al., *Biochemistry* 36:650–659 (1997)). Thus phosphoramidates are able to mimic many of the properties of RNA that are important for molecular recognition.

Example 3

*Candida albicans* Results

C-10/1x is a *Candida albicans* rRNA Group I ribozyme. Dissociation constants for 5' exon oligonucleotide mimics which bind to the C-10/1x ribozyme were measured by competitive band-shift native electrophoresis using methods described in Testa et al., *Biochemistry* 37:9379–9385 (1998). The results for a variety of oligonucleotides complementary or containing a one base mismatch to the C-10/1x 5' exon guide sequence are shown in Table 2.

TABLE 2

Thermodynamic Parameters for Oligonucleotide Binding to C-10/1x and r(GGAGGC) in H15 Mg buffer[a].

| | Binding to C-10/1x | | Binding to r(GGAGGC) | | Tertiary Stability | |
| --- | --- | --- | --- | --- | --- | --- |
| Oligo[b] | $K_d$,C-10/1x (nM) | $\Delta G°37$,C-10/1x (kcal/mol)[c] | $K_{d,B.P.}$ (mM)[c] | $\Delta G°37$,B.P. (kcal/mol) | $\Delta\Delta G°37$,BETI (kcal/mol)[d] | BETI[e] |
| r(GCCUCU) [Seq ID No:7] | 0.7 | −13.0 | 0.1 | −8.5 | −4.5 | 1500 |
| r(GACUCU) [Seq ID No:8] | 6.9 | −11.6 | 0.6 | −2.1 | −9.5 | 4800000 |

TABLE 2-continued

Thermodynamic Parameters for Oligonucleotide
Binding to C-10/1x and r(GGAGGC) in H15 Mg buffer[a].

| | Binding to C-10/1x | | Binding to r(GGAGGC) | | Tertiary Stability | |
|---|---|---|---|---|---|---|
| Oligo[b] | $K_d$,C-10/1x (nM) | $\Delta G°_{37}$,C-10/1x (kcal/mol)[c] | $K_{d,B.P.}$ (mM)[c] | $\Delta G°_{37}$,B.P. (kcal/mol) | $\alpha\alpha G°_{37}$,BETI (kcal/mol)[d] | BETI[e] |
| m(GCCUC)rU [Seq ID No:3] | 1.0 | −12.9 | $1.8 \times 10^{-3}$ | −11 | −1.9 | 20 |
| m(GACUC)rU [Seq ID No:4] | 6.3 | −11.6 | 0.1 | −5.6 | −6.1 | 20000 |
| dn(GCCTC)rU [Seq ID No:2] | 2.5 | −12.2 | $1.8 \times 10^{-3}$ | −11.0 | −1.2 | 7 |
| dns(GCCTC)rU [Seq ID No:9] | 2.0 | −12.3 | $1.4 \times 10^{-4f}$ | $-9.7^f$ | $-2.6^f$ | $72^f$ |

[a]H15Mg buffer consists of 50 mM Hepes (25 mM Na$^+$), 15 mM MgCl$_2$, and 135 mM KCl at pH 7.5.
[b]r = RNA, dn = deoxyphosphoramidate, rn = ribophosphoramidate, and dns = deoxythiophosphoramidate.
[c]Calculated from $\Delta G°_{37}$ = RTln($K_d$) where R = 0.001987 kcal mol$^{-1}$K$^{-1}$ and T = 310 K, using more significant digits than listed in this table.
[d]Free energy increment form tertiary interactions calculated from the difference in $\Delta G°_{37}$ values for binding to C-10/1x and r(GGAGGC).
[e]Binding enhanced by tertiary interactions (BETI) was calculated using Kd values containing more significant digits than those listed in this table. For description of BETI see Testa et al., Biochemistry 36:15303–15314 (1997).
[f]Values are estimates because the thermodynamic melts were not two-state.

The results in Table 2 demonstrate that a (dG)n(dC)n(dC)n(dT)n(dC)n(rU) [Seq. ID No:2] phosphoramidate oligonucleotide that is similar to the 5' exon guide sequence of C-10/1x ribozyme from *C. albicans* binds in a stable fashion to the C-10/1x ribozyme. Further, inspection of the thermodynamic properties measured in Table 2, show that the stability of binding of the phosphoramidate oligonucleotides ([Seq ID No:2], [Seq ID No:3] and [Seq ID No:9]) to the C-10/1x ribozyme is primarily due to a large increase in the stability of base-pairing ($K_{d, B.P.}$) as compared to the corresponding RNA oligonucleotide ([Seq ID No:7]).

Figure 5:
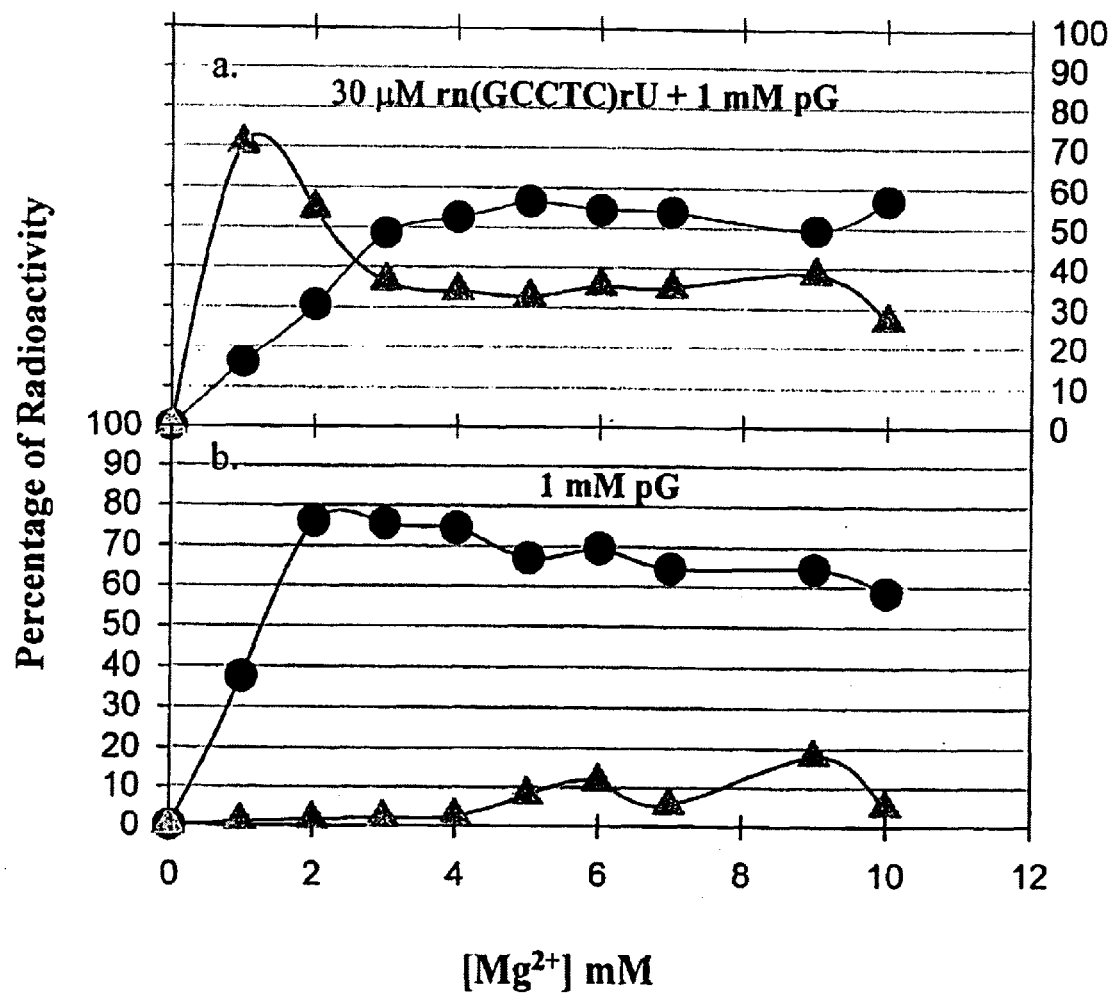
FIG. 5 shows graphical representations of the magnesium dependence of the formation of spliced products from internally radiolabeled *C. albicans* precursor. Reactions were run for 1 h in HxMg buffer, consisting of 50 mM Hepes (25 mM Na$^+$) at pH 7.5, 135 mM KCl, and x mM MgCl$_2$, where x is listed below the plots. Each plot is the average of two independently run self-splice gel assays, and the error of each point is typically ±6% of the average value. Circles represent the 5' exon-3' exon product generated by cis-splicing. Triangles represent the hexamer-3' exon product formed by trans-splicing. Results are shown (A) in the presence of 1 mM pG and 30 μM (dG)n(dC)n(dC)n(dT)n(dC)n(rU) [Seq. ID. No:2], and (B) in the absence of added hexamer.
Figure 6:
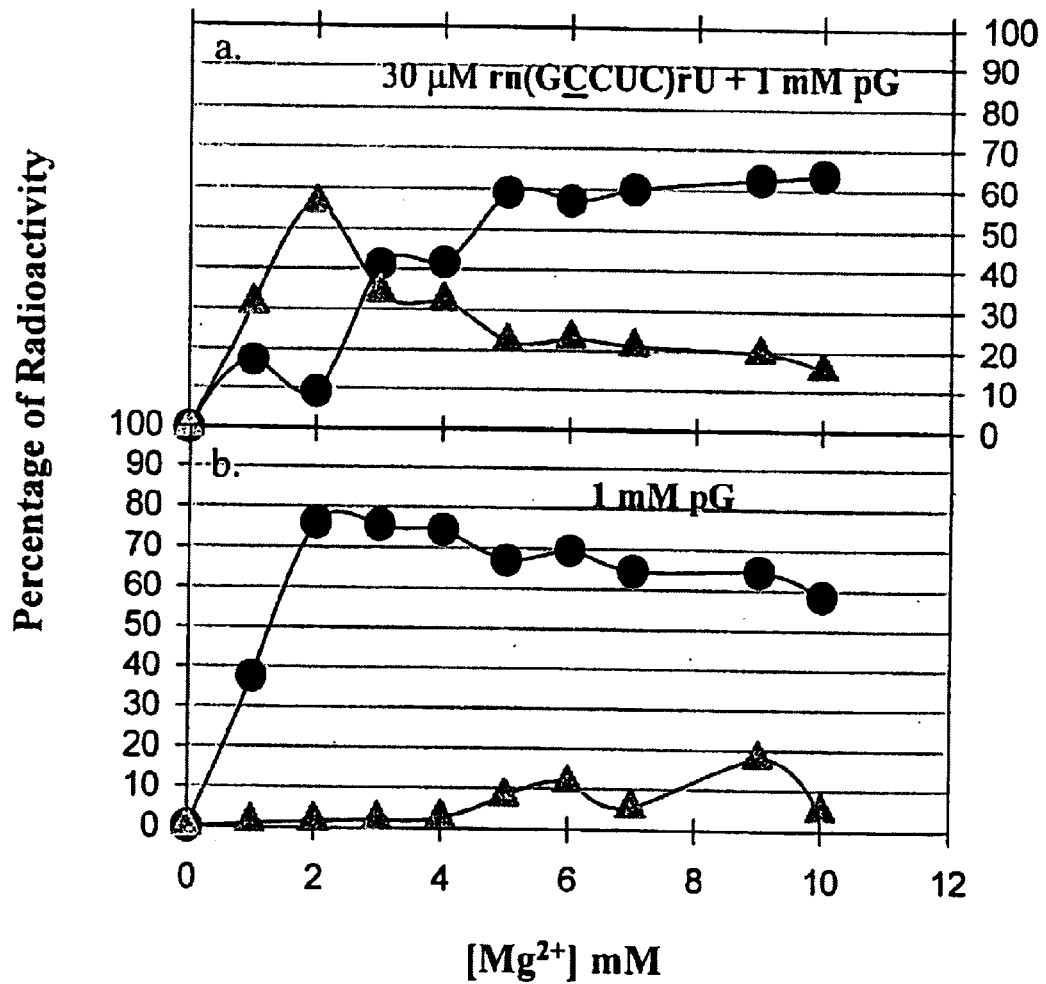
FIG. 6 shows graphical representations of the magnesium dependence of the formation of spliced products from internally radiolabeled *C. albicans* precursor. Reactions were run for 1 h in HxMg buffer, consisting of 50 mM Hepes (25 mM Na$^+$) at pH 7.5, 135 mM KCl, and x mM MgCl$_2$, where x is listed below the plots. Each plot is the average of two independently run self-splice gel assays, and the error of each point is typically ±6% of the average value. Circles represent the 5' exon-3' exon product generated by cis-splicing. Triangles represent the hexamer-3' exon product formed by trans-splicing. Results are shown (A) in the presence of 1 mM pG and 30 μM (rG)n(rC)n(rC)n(rT)n(rC)n(rU) [Seq. ID. No:3], and (B) in the absence of added hexamer.
Figure 7:
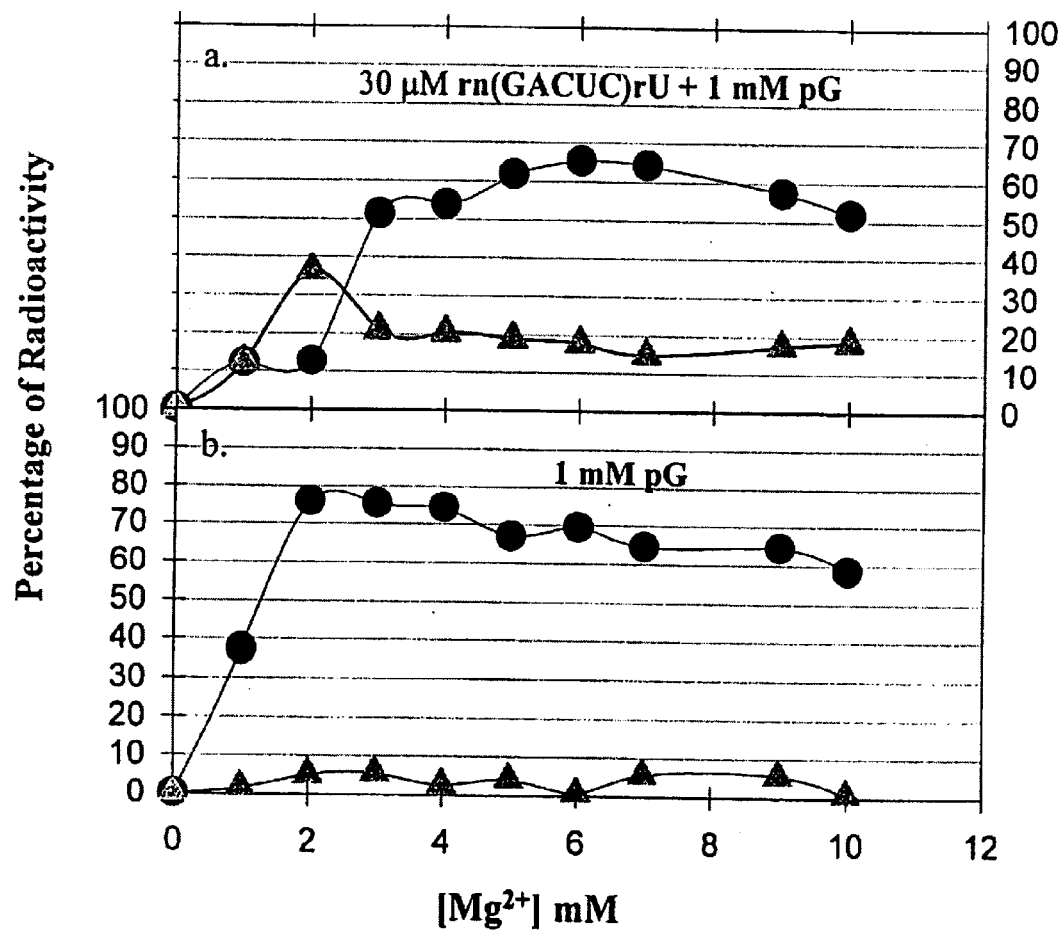
FIG. 7 shows graphical representations of the magnesium dependence of the formation of spliced products from internally radiolabeled *C. albicans* precursor. Reactions were run for 1 h in HxMg buffer, consisting of 50 mM Hepes (25 mM Na$^+$) at pH 7.5, 135 mM KCl, and x mM MgCl$_2$, where x is listed below the plots. Each plot is the average of two independently run self-splice gel assays, and the error of each point is typically ±6% of the average value. Circles represent the 5' exon-3' exon product generated by cis-splicing. Triangles represent the hexamer-3' exon product formed by trans-splicing. Results are shown (A) in the presence of 1 mM pG and 30 μM (rG)n(rA)n(rC)n(rT)n(rC)n(rU) [Seq. ID. No:4], and (B) in the absence of added hexamer.

The effects of [Mg$^{2+}$] on the formation of various products derived from internally radiolabeled precursor RNA (C-10/1x ribozyme) in the presence and absence of 30 μm (dG)n(dC)n(dC)n(dT)n(dC)n(rU) [Seq. ID No:2], 30 μm (rG)n(rC)n(rC)n(rU)n(rC)n(rU) [Seq. ID No:4], 30 μm (rG)n(rA)n(rC)n(rU)n(rC)n(rU) [Seq. ID No:4] and 1 mM pG are shown in FIGS. 5, 6 and 7, respectively. FIG. 5A shows that in the presence of (dG)n(dC)n(dC)n(dT)n(dC)n(rU) [Seq. ID No:2] and pG, the hexamer-3' exonproduct (trans-splicing) reaches a maximum at 1 mM Mg$^{2+}$, where it is about 5-fold more prevalent than the completely excised intron product (cis-splicing). FIG. 5B shows the amounts of cis- and trans-splicing products formed in the presence of 1 mM pG and no (dG)n(dC)n(dC)n(dT)n(dC)n(rU) [Seq. ID No:2] oligonucleotide. As noted for *P. carinii*, suicide splicing (Example 2), increasing the Mg$^{2+}$ concentration just a little (here to above 3 mM Mg$^{2+}$) results in a predominance of 5' exon-3' exon product (cis-splicing) (FIG. 5A). Experiments were performed to determine the oligonucleotide concentration dependence of trans-verses cis-splicing at 1 mM Mg$^{2+}$ and 2 mM Mg$^{2+}$ for (dG)n(dC)n(dC)n(dT)n(dC)n(rU) [Seq. ID No:2]. Trans-splicing of the model precursor *C. albicans* Group I precursor rRNA was found to predominate at oligonucleotide concentration greater than about 200 nM at 1 mM Mg$^{2+}$ and at about 1000 nM at 2 mM Mg$^{2+}$ (data not shown). In both cases, the amount of suicide trans-splicing product continued to increase as the concentration of (dG)n(dC)n(dC)n(dT)n(dC)n(rU) [Seq. ID No:2] oligonucleotide was increased beyond the above noted threshold values. At lower oligonucleotide concentrations the cis-splice product predominated.

FIGS. 6 and 7 show analogous results for the Mg$^{2+}$ dependence of splicing of a *C. albicans* model precusor rRNA in the presence of 30 μm of ribophosphoramidate oligonucleotide (rG)n(rC)n(rC)n(rU)n(rC)n(rU) [Seq. ID No:3] and internal guide sequence mismatch ribophosphoramidate oligonucleotide (rG)n(rA)n(rC)n(rU)n(rC)n(rU) [Seq. ID No:4], respectively. The results in FIG. 6A show that in the presence of (rG)n(rC)n(rC)n(rU)n(rC)n(rU) [Seq. ID No:3] and pG, the 5' exon-intron product (trans-splicing) reaches a maximum at 2 nM Mg$^{2+}$, where it is about 5-fold more prevalent than the 5' exon-3' exon product (cis-splicing). When the 5' exon guide sequence one base mismatch ribophosphoramidate oligonucleotide (rG)n(rA)n(rC)n(rU)n(rC)n(rU) [Seq. ID No:4] is used, a peak of trans splicing product is still observed a 2 mM Mg$^{2+}$, however, now the trans splicing product is only about 3-fold more prevalent than the 5' exon-3' exon product (FIG. 6).

The oligonucleotide concentration dependence of trans-verses cis-splicing at 1 mM Mg$^{2+}$ and 2 mM Mg$^{2+}$ was measure for (rG)n(rC)n(rC)n(rT)n(rC)n(rU) [Seq. ID No:3]. Trans-splicing of the *C. albicans* Group I precursor RNA was found to predominate at oligonucleotide concentration greater than about 100 nM at 1 mM Mg$^{2+}$ and at about 1000 nM at 2 mM Mg$^{2+}$ (data not shown). With both concentrations of Mg$^{2+}$, the amount of suicide trans-splicing product continued to increase as the concentration of (rG)n(rC)n(rC)n(rT)n(rC)n(rU) [Seq. ID No:3] oligonucleotide was increased. Similarly, below the above noted threshold oligonucleotide concentrations the amount of cis-splicing product predominated at both Mg$^{2+}$ concentrations.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An inhibitor of a Group I intron self-splicing reaction comprising an oligonucleotide having a polynucleotide sequence that binds to a 5' internal guide sequence of a precursor RNA containing a Group I intron, or to a portion thereof, wherein said oligonucleotide binds to the 5' internal guide sequence of the precursor RNA and trans-splices to the 3' exon of the precursor RNA, and wherein said oligonucleotide comprises at least one polynucleotide sequence chosen from SEQ ID No:1, SEQ ID No:2, SEQ ID No:3, and SEQ ID No:9.

2. The inhibitor of claim 1 wherein said oligonucleotide comprises the polynucleotide sequence of SEQ ID No:1 and wherein said precursor RNA is a precursor ribosomal RNA from *Pneumocystis carinii*.

3. The inhibitor of claim 1 wherein said oligonucleotide comprises at least one polynucleotide sequence chosen from SEQ ID No:2, SEQ ID No:3, and SEQ ID No:9 and wherein said precursor RNA is a precursor ribosomal RNA from *Candida albicans*.

4. A composition comprising a suicide inhibitor of claim 1, together with a pharmaceutically acceptable carrier.

5. A method of inhibiting self-splicing of a Group I intron comprising contacting a precursor RNA containing a Group I intron with an oligonucleotide, wherein said oligonucleotide trans-splices to a 3' exon sequence of said precursor RNA and inhibits self-splicing of the Group I intron.

6. The method of claim 5 wherein said oligonucleotide comprises deoxynucleotides, ribonucleotides, or a combination thereof, and said oligonucleotide comprises a 3' terminal ribonucleoside.

7. The method of claim 5 wherein said oligonucleotide contains at least one N3'→P5' phosphoramidate or N3'→P5' thiophosphoramidate linkage.

8. The method of claim 5 wherein said oligonucleotide comprises at least one polynucleotide sequence chosen from SEQ ID No:1, SEQ ID No:2, SEQ ID No:3 and SEQ ID No:9.

9. The method of claim 5 wherein said oligonucleotide comprises the polynucleotide of SEQ ID No:1 and wherein said precursor RNA is a precursor ribosomal RNA from *Pneumocystis carinii*.

10. The method of claim 5 wherein said oligonucleotide comprises at least one polynucleotide sequence chosen from SEQ ID No:2, SEQ ID No:3, and SEQ ID No:9 and wherein said precursor RNA is a precursor ribosomal RNA from *Candida albicans*.

11. A method for inhibiting the growth of an organism transcribing a precursor RNA containing a Group I intron comprising contacting said organism with an amount of an oligonucleotide effective for growth inhibition, wherein said oligonucleotide trans-splices to a 3' exon sequence of said precursor RNA and inhibits self-splicing of the Group I intron, wherein inhibition of self-splicing of the Group I intron inhibits the growth of the organism.

12. The method of claim 11 wherein said oligonucleotide comprises deoxynucleotides, ribonucleotides, or a combination thereof, and said oligonucleotide comprises a 3' terminal ribonucleoside.

13. The method of claim 11 wherein said oligonucleotide comprises at least one N3'→P5' phosphoramidate or thiophosphoramidate linkage.

14. The method of claim 11 wherein said oligonucleotide comprises at least one polynucleotide sequence chosen from SEQ ID No: 1, SEQ ID No:2, SEQ ID No:3 and SEQ ID No:9.

15. The method of claim 11 wherein said oligonucleotide comprises the polynucleotide of SEQ ID No:1 and wherein said precursor RNA is a precursor ribosomal RNA from *Pneumocystis carinii*.

16. The method of claim 11 wherein said oligonucleotide comprises at least one polynucleotide sequence chosen from SEQ ID No:2, SEQ ID No:3, and SEQ ID No:9 and wherein said precursor RNA is a precursor ribosomal RNA from *Candida albicans*.

17. A method of designing an inhibitor of Group I intron splicing comprising choosing a nucleotide sequence that binds to a 5' internal guide sequence present in precursor RNA containing a Group I intron, or to a portion thereof, and preparing an oligonucleotide having the chosen sequence, wherein said oligonucleotide binds to the 5' internal guide sequence of the precursor RNA and trans-splices to the 3' exon of the precursor RNA.

18. The method of claim 17 wherein said oligonucleotide comprises deoxynucleotides, ribonucleotides, or a combination thereof, and said oligonucleotide comprises a 3' terminal ribonucleoside.

19. The method of claim 17 wherein said oligonucleotide contains at least one N3'→P5' phosphoramidate or thiophosphoramidate linkage.

* * * * *